United States Patent
Park et al.

(10) Patent No.: US 8,008,448 B2
(45) Date of Patent: Aug. 30, 2011

(54) COTININE NEUTRALIZING ANTIBODY

(75) Inventors: Sunyoung Park, Seoul (KR); Junho Chung, Seoul (KR); Dohoon Lee, Gyeonggi-do (KR); Jae-Gahb Park, Seoul (KR)

(73) Assignee: National Cancer Center, Goyang-si (KR)

( * ) Notice: Subject to any disclaimer, the term of this patent is extended or adjusted under 35 U.S.C. 154(b) by 441 days.

(21) Appl. No.: 12/048,636

(22) Filed: Mar. 14, 2008

(65) Prior Publication Data

US 2008/0226650 A1   Sep. 18, 2008

Related U.S. Application Data

(60) Provisional application No. 60/894,891, filed on Mar. 14, 2007.

(51) Int. Cl.
*C07K 16/00* (2006.01)
*C07K 16/46* (2006.01)

(52) U.S. Cl. ............. 530/388.1; 530/388.24; 530/387.3; 530/387.1

(58) Field of Classification Search .................. None
See application file for complete search history.

(56) References Cited

FOREIGN PATENT DOCUMENTS
EP        0194158 A2 *  3/1988

OTHER PUBLICATIONS

Janeway et al. Immunology, 3$^{rd}$ Ed., Garland Press, 1997, p. 3:7-3:11.*
Fundamental Immunology, William E. Paul, MD 3$^{rd}$ Ed., 1993, p. 242.*
Portolano et al. J. Immunology, 1993, vol. 150, p. 880-887.*

* cited by examiner

*Primary Examiner* — Yunsoo Kim
(74) *Attorney, Agent, or Firm* — Joseph H. Kim; JHK Law

(57) ABSTRACT

The present application discloses monoclonal antibody against cotinine and nicotine.

4 Claims, 5 Drawing Sheets

FIG. 1
(A)
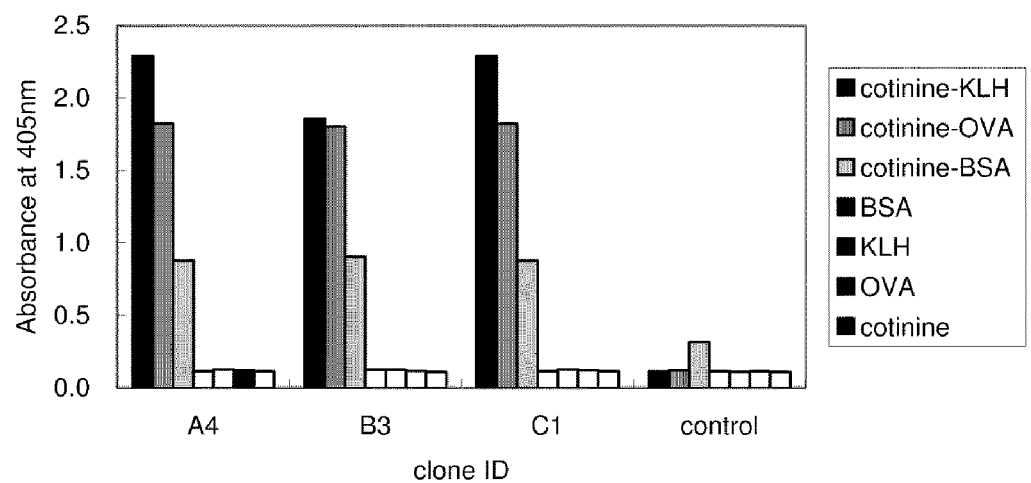
(B)
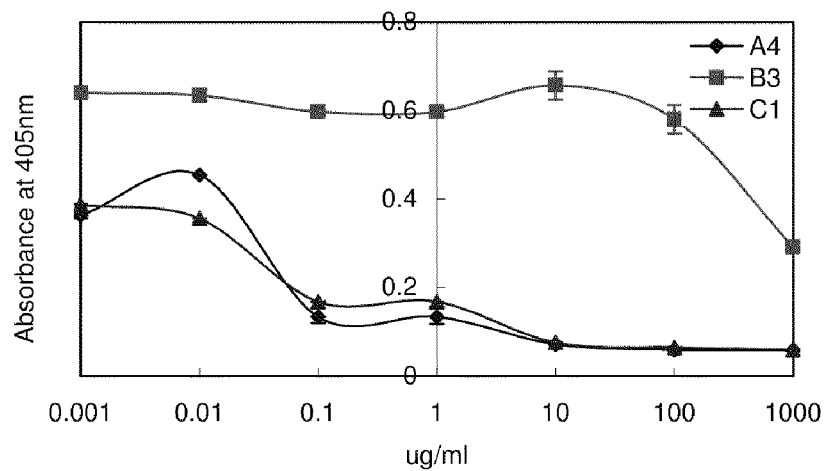

FIG. 2

Heavy chain

```
              FR1                CDR1         FR2                 CDR2
A4  GQSLEESGGRLVTPGGSLTLTCTASGFSLS-SDWMN-WVRQAPGKGLEWIG-AVSRGSSGSTYYATWTK
B3  QQQLVESGGGLVTPGGTLTLTCTASGFSLS-SYDMI-WVRQAPGKGLEYIG-FISTGAA   TYYASWAR
C1  QQQLVESGGRLVTPGGSLTLTCTASGFSLN-NYWMS-WVRQAPGKGLEWIG-DIHGNRGFNYH ASWAK
                FR3                   CDR3           FR4
A4  GRFTISKTSSTTVTLTVTDLQPSDTATYFCAR-IPYFGYNNGDI-WGPGTLVTVSS (SEQ ID NO:19)
B3  GRFTISRTS TTVDLKVTSLTTEDTATYFCAR-WDGSTIDNI  -WGPGTLVTVSS (SEQ ID NO:20)
C1  GRFTVSRTS TTVDLRMTSLTTEDTAIYFCAR-ADDSGSHDI  -WGPGTLVTVSS (SEQ ID NO:21)
```

Light chain

```
             FR1                   CDR1              FR2                CDR2
A4  ELDLTQTPSATSAAVGGTVTINC-QSSQSLYGNEWLS-WYQQKPGQSPKVLIS-RISTLAS
B3  ELVMTQTPSSVSAAVGGTVTINC-QASQSVYKNNYLS-WFQQKPGQPPKLLIY-LASTLAS
C1  ELDLTQTPSPVSAAVGDTVTINC-QSSQSVYSAK LS-WYQQKPGQPPKLLIY-YGSTLAS
                FR3                    CDR3              FR4
A4  GVPSRFKGSGSGTQFTLTIRDLECGDAATYYC-AGGYNFGLFPFG  -GGTEVVVKR (SEQ ID NO:22)
B3  GVSSRFKGSGSGTQFTLTISGVQREDAATYYC-AGYRYTTVDATAFG-GGTEVVVKR (SEQ ID NO:23)
C1  GVPSRFKGSGSGTQFSLTISDVQCADAATYYC-QGTYYGPDWYFAFG-GGTEVVVKR (SEQ ID NO:24)
```

FIG. 3
(A)
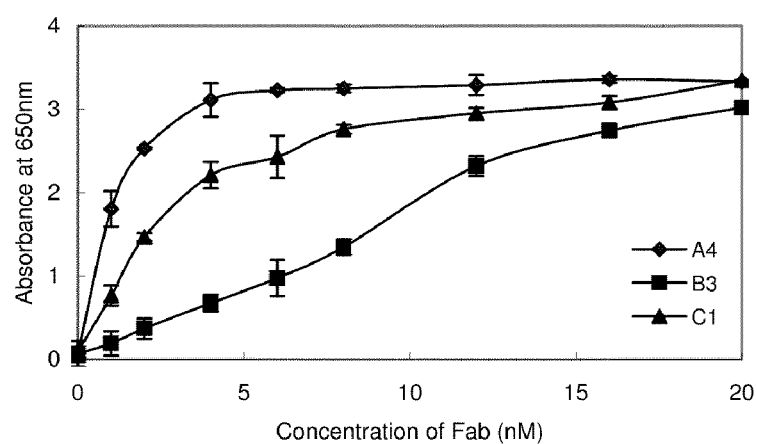
(B)
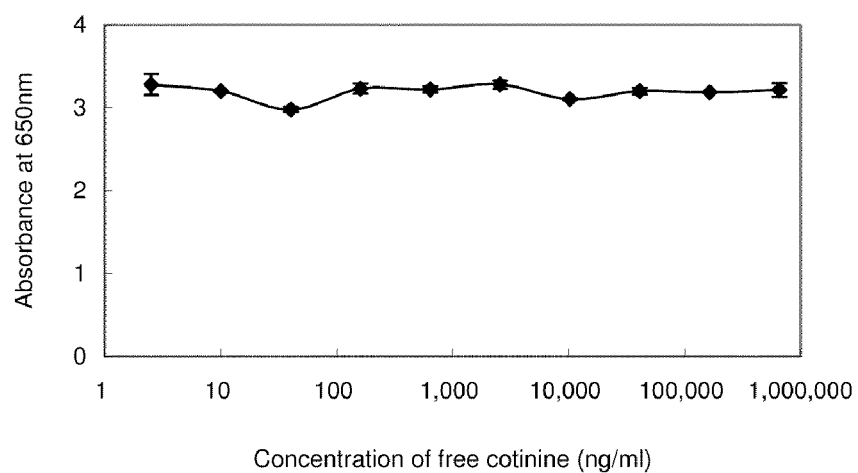

FIG. 3
(C)
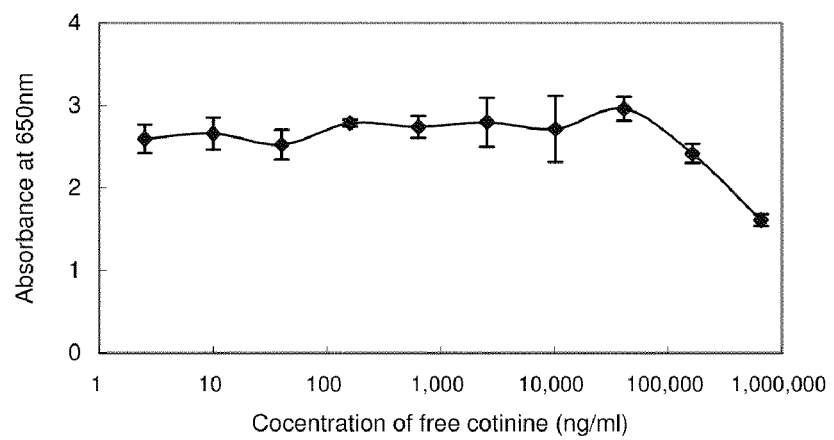
(D)
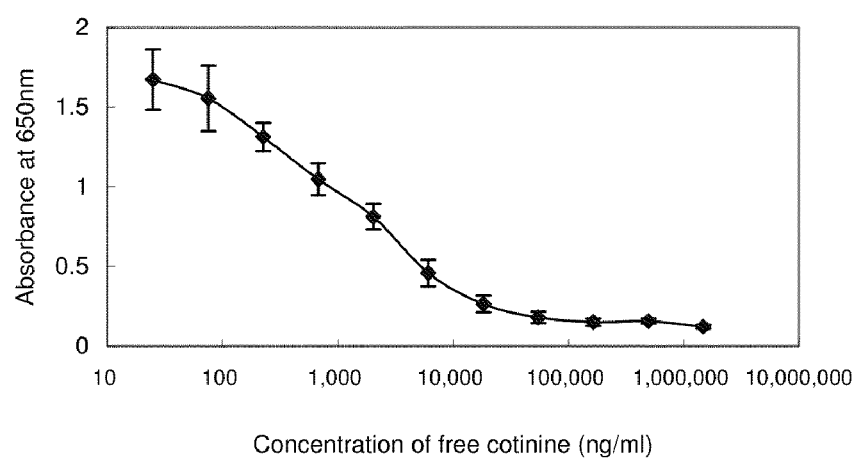

(E)

SEQUENCE LISTING

```
<160> NUMBER OF SEQ ID NOS: 24

<210> SEQ ID NO 1
<211> LENGTH: 5
<212> TYPE: PRT
<213> ORGANISM: Artificial Sequence
<220> FEATURE:
<223> OTHER INFORMATION: CDR1

<400> SEQUENCE: 1

Ser Asp Trp Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: CDR2

<400> SEQUENCE: 2
```

Ala Val Ser Arg Gly Ser Ser Gly Ser Thr Tyr Tyr Ala Thr Trp Thr
1               5                   10                  15

Lys

<210> SEQ ID NO 3
<211> LENGTH: 11
<212> TYPE: PRT
<213> ORGANISM: Artificial Sequence
<220> FEATURE:
<223> OTHER INFORMATION: CDR3

<400> SEQUENCE: 3

Ile Pro Tyr Phe Gly Tyr Asn Asn Gly Asp Ile
1               5                   10

<210> SEQ ID NO 4
<211> LENGTH: 13
<212> TYPE: PRT
<213> ORGANISM: Artificial Sequence
<220> FEATURE:
<223> OTHER INFORMATION: CDR1

<400> SEQUENCE: 4

Gln Ser Ser Gln Ser Leu Tyr Gly Asn Glu Trp Leu Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDR2

<400> SEQUENCE: 5

Arg Ile Ser Thr Leu Ala Ser
1               5

<210> SEQ ID NO 6
<211> LENGTH: 12
<212> TYPE: PRT
<213> ORGANISM: Artificial Sequence
<220> FEATURE:
<223> OTHER INFORMATION: CDR3

<400> SEQUENCE: 6

Ala Gly Gly Tyr Asn Phe Gly Leu Phe Pro Phe Gly
1               5                   10

<210> SEQ ID NO 7
<211> LENGTH: 5
<212> TYPE: PRT
<213> ORGANISM: Artificial Sequence
<220> FEATURE:
<223> OTHER INFORMATION: CDR1

<400> SEQUENCE: 7

Ser Tyr Asp Met Ile
1               5

<210> SEQ ID NO 8
<211> LENGTH: 15
<212> TYPE: PRT
<213> ORGANISM: Artificial Sequence
<220> FEATURE:
<223> OTHER INFORMATION: CDR2

<400> SEQUENCE: 8

```
Phe Ile Ser Thr Gly Ala Ala Thr Tyr Tyr Ala Ser Trp Ala Arg
1               5                   10                  15

<210> SEQ ID NO 9
<211> LENGTH: 9
<212> TYPE: PRT
<213> ORGANISM: Artificial Sequence
<220> FEATURE:
<223> OTHER INFORMATION: CDR3

<400> SEQUENCE: 9

Trp Asp Gly Ser Thr Ile Asp Asn Ile
1               5

<210> SEQ ID NO 10
<211> LENGTH: 13
<212> TYPE: PRT
<213> ORGANISM: Artificial Sequence
<220> FEATURE:
<223> OTHER INFORMATION: CDR1

<400> SEQUENCE: 10

Gln Ala Ser Gln Ser Val Tyr Lys Asn Asn Tyr Leu Ser
1               5                   10

<210> SEQ ID NO 11
<211> LENGTH: 7
<212> TYPE: PRT
<213> ORGANISM: Artificial Sequence
<220> FEATURE:
<223> OTHER INFORMATION: CDR2

<400> SEQUENCE: 11

Leu Ala Ser Thr Leu Ala Ser
1               5

<210> SEQ ID NO 12
<211> LENGTH: 14
<212> TYPE: PRT
<213> ORGANISM: Artificial Sequence
<220> FEATURE:
<223> OTHER INFORMATION: CDR3

<400> SEQUENCE: 12

Ala Gly Tyr Arg Tyr Thr Thr Val Asp Ala Thr Ala Phe Gly
1               5                   10

<210> SEQ ID NO 13
<211> LENGTH: 5
<212> TYPE: PRT
<213> ORGANISM: Artificial Sequence
<220> FEATURE:
<223> OTHER INFORMATION: CDR1

<400> SEQUENCE: 13

Asn Tyr Trp Met Ser
1               5

<210> SEQ ID NO 14
<211> LENGTH: 16
<212> TYPE: PRT
<213> ORGANISM: Artificial Sequence
<220> FEATURE:
<223> OTHER INFORMATION: CDR2

<400> SEQUENCE: 14

Asp Ile His Gly Asn Arg Gly Phe Asn Tyr His Ala Ser Trp Ala Lys
```

```
<210> SEQ ID NO 15
<211> LENGTH: 9
<212> TYPE: PRT
<213> ORGANISM: Artificial Sequence
<220> FEATURE:
<223> OTHER INFORMATION: CDR3

<400> SEQUENCE: 15

Ala Asp Asp Ser Gly Ser His Asp Ile
1               5

<210> SEQ ID NO 16
<211> LENGTH: 12
<212> TYPE: PRT
<213> ORGANISM: Artificial Sequence
<220> FEATURE:
<223> OTHER INFORMATION: CDR1

<400> SEQUENCE: 16

Gln Ser Ser Gln Ser Val Tyr Ser Ala Lys Leu Ser
1               5                   10

<210> SEQ ID NO 17
<211> LENGTH: 7
<212> TYPE: PRT
<213> ORGANISM: Artificial Sequence
<220> FEATURE:
<223> OTHER INFORMATION: CDR2

<400> SEQUENCE: 17

Tyr Gly Ser Thr Leu Ala Ser
1               5

<210> SEQ ID NO 18
<211> LENGTH: 14
<212> TYPE: PRT
<213> ORGANISM: Artificial Sequence
<220> FEATURE:
<223> OTHER INFORMATION: CDR3

<400> SEQUENCE: 18

Gln Gly Thr Tyr Tyr Gly Pro Asp Trp Tyr Phe Ala Phe Gly
1               5                   10

<210> SEQ ID NO 19
<211> LENGTH: 5
<212> TYPE: PRT
<213> ORGANISM: Artificial Sequence
<220> FEATURE:
<223> OTHER INFORMATION: CDR1

<400> SEQUENCE: 19

Arg Asp Trp Met Asn
1               5

<210> SEQ ID NO 20
<211> LENGTH: 15
<212> TYPE: PRT
<213> ORGANISM: Artificial Sequence
<220> FEATURE:
<223> OTHER INFORMATION: CDR2

<400> SEQUENCE: 20

Ala Ile Gly Arg Ser Gly Asp Thr Tyr Tyr Ala Thr Trp Ala Lys
1               5                   10                  15
```

```
<210> SEQ ID NO 21
<211> LENGTH: 11
<212> TYPE: PRT
<213> ORGANISM: Artificial Sequence
<220> FEATURE:
<223> OTHER INFORMATION: CDR3

<400> SEQUENCE: 21

Ile Pro Tyr Phe Gly Trp Asn Asn Gly Asp Ile
1               5                   10

<210> SEQ ID NO 22
<211> LENGTH: 13
<212> TYPE: PRT
<213> ORGANISM: Artificial Sequence
<220> FEATURE:
<223> OTHER INFORMATION: CDR1

<400> SEQUENCE: 22

Gln Ser Ser Gln Ser Pro Tyr Ser Asn Glu Trp Leu Ser
1               5                   10

<210> SEQ ID NO 23
<211> LENGTH: 7
<212> TYPE: PRT
<213> ORGANISM: Artificial Sequence
<220> FEATURE:
<223> OTHER INFORMATION: CDR2

<400> SEQUENCE: 23

Arg Ile Ser Thr Leu Ala Ser
1               5

<210> SEQ ID NO 24
<211> LENGTH: 12
<212> TYPE: PRT
<213> ORGANISM: Artificial Sequence
<220> FEATURE:
<223> OTHER INFORMATION: CDR3

<400> SEQUENCE: 24

Ala Gly Gly Tyr Asn Phe Gly Leu Phe Pro Phe Gly
1               5                   10
```

COTININE NEUTRALIZING ANTIBODY

CROSS-REFERENCE TO RELATED APPLICATIONS

The present application claims the benefit of priority to U.S. Provisional Application No. 60/894,891, filed Mar. 14, 2007, the contents of which are incorporated by reference herein in their entirety.

BACKGROUND OF THE INVENTION

1. Field of the Invention

The present invention relates to antibody specific for cotinine, and antibody specific for nicotine. The present invention also relates to the field of treating nicotine addiction.

2. General Background and State of the Art

Nicotine is a naturally occurring alkaloid found in many plants. The principal source of nicotine exposure is through the use of tobacco. Nicotine is an amine composed of pyridine and pyrrolidine rings and crosses biological membranes and the blood brain barrier easily. The absorbed nicotine is extensively metabolized in the liver to form a wide variety of metabolites by the mixed function of oxidase system. Though nicotine has been shown to affect a wide variety of biological functions ranging from gene expression to regulation of hormone secretion and enzyme activities, nicotine is known to induce addiction. But nicotine has a relatively short half-life, approximately 2 hours, which is not sufficient to induce immunogenicity.

Cotinine is the principal proximate metabolite of nicotine, and 70~80% of nicotine absorbed is converted to cotinine prior to metabolizing into other metabolites in the liver, has a half-life of approximately 20 hours. Cotinine can be measured in a number of biological fluids including blood, saliva, urine, semen and cervical exudates. Cotinine is sufficiently sensitive to be detected also in the body fluids of those individuals, exposed to passive or environment tobacco smoke and this was why cotinine-antibody was made first and it showed the possibility of cross-reactivity for nicotine. Furthermore, in particular by gene modification of heavy chain CDR3 (HCDR3), nicotine-specific antibody can be produced from cotinine-specific antibody.

In the present study, we for the first time generated a rabbit/human chimeric monoclonal antibody specific to cotinine that contains rabbit heavy chain ($V_H$) and light chain ($V_L$) variable domain and human heavy chain ($C_{H1}$) and light chain ($C_L$) constant domain from the synthesized antibody library. This antibody also shows cross-reactivity with nicotine and these results indicate generation of antibody that is specific to nicotine only by the modification of the HCDR3 gene. The present invention provides a therapeutic monoclonal antibody to treat nicotine addiction.

SUMMARY OF THE INVENTION

Nicotine plays a key role in tobacco-mediated-nicotine addiction. Thus, the need for therapeutic antibody, specific to nicotine for preclinical and clinical study, is urgently required. Rabbit was immunized with cotinine-BSA conjugate and rabbit/human chimeric antibody library was generated. Using phage display, four clones A4, B3, C1 and SUN10, specific to cotinine were isolated from the synthesized library, and the selected antibody exhibited strong affinity to cotinine and also showed cross-reactivity to nicotine. And it was confirmed that binding of B3 clone to cotinine BSA is reduced by the presence of soluble nicotine in competition enzyme immunoassay. Applicant has disclosed for the first time a recombinant monoclonal antibody that is specific to both cotinine and nicotine, which can potently inhibit tobacco-mediated-nicotine addiction.

In one aspect, the invention is directed to a monoclonal antibody specific for cotinine and/or nicotine. The monoclonal antibody may have an amino acid sequence in the heavy chain variable region in the CDR1 region selected from SEQ ID NO:1, SEQ ID NO:7, SEQ ID NO:13, and SEQ ID NO:19. The monoclonal antibody may have an amino acid sequence in the heavy chain variable region in the CDR2 region selected from SEQ ID NO:2, SEQ ID NO:8, SEQ ID NO:14, and SEQ ID NO:20. The monoclonal antibody may have an amino acid sequence in the heavy chain variable region in the CDR3 region selected from SEQ ID NO:3, SEQ ID NO:9, SEQ ID NO:15, and SEQ ID NO:21.

The inventive monoclonal antibody may have an amino acid sequence in the heavy chain variable region comprised of the following:

(i) in the CDR1 region, SEQ ID NO:1, SEQ ID NO:7, SEQ ID NO:13, or SEQ ID NO:19;
(ii) in the CDR2 region, SEQ ID NO:2, SEQ ID NO:8, SEQ ID NO:14, or SEQ ID NO:20; and
(iii) in the CDR3 region, SEQ ID NO:3, SEQ ID NO:9, SEQ ID NO:15, or SEQ ID NO:21.

The monoclonal antibody may have an amino acid sequence in the light chain variable region in the CDR1 region selected from SEQ ID NO:4, SEQ ID NO:10, SEQ ID NO:16, and SEQ ID NO:22. The monoclonal antibody may have an amino acid sequence in the light chain variable region in the CDR2 region selected from SEQ ID NO:5, SEQ ID NO:11, SEQ ID NO:17, and SEQ ID NO:23. The monoclonal antibody may have an amino acid sequence in the light chain variable region in the CDR3 region selected from SEQ ID NO:6, SEQ ID NO:12, SEQ ID NO:18, and SEQ ID NO:24.

The monoclonal antibody may have an amino acid sequence in the light chain variable region comprised of the following:

(i) in the CDR1 region, SEQ ID NO:4, SEQ ID NO:10, SEQ ID NO:16, or SEQ ID NO:22;
(ii) in the CDR2 region, SEQ ID NO:5, SEQ ID NO:11, SEQ ID NO:17, or SEQ ID NO:23; and
(iii) in the CDR3 region, SEQ ID NO:6, SEQ ID NO:12, SEQ ID NO:18, or SEQ ID NO:24.

In another aspect, the monoclonal antibody may have an amino acid sequence in the heavy chain variable region, which is selected from the group consisting of:

(i) in the CDR1 region, SEQ ID NO:1, SEQ ID NO:7, SEQ ID NO:13, or SEQ ID NO:19;
(ii) in the CDR2 region, SEQ ID NO:2, SEQ ID NO:8, SEQ ID NO:14, or SEQ ID NO:20; and
(iii) in the CDR3 region, SEQ ID NO:3, SEQ ID NO:9, SEQ ID NO:15, or SEQ ID NO:21, and an amino acid sequence in the light chain variable region, which is selected from the group consisting of:

(i) in the CDR1 region, SEQ ID NO:4, SEQ ID NO:10, SEQ ID NO:16, or SEQ ID NO:22;
(ii) in the CDR2 region, SEQ ID NO:5, SEQ ID NO:11, SEQ ID NO:17, or SEQ ID NO:23; and
(iii) in the CDR3 region, SEQ ID NO:6, SEQ ID NO:12, SEQ ID NO:18, or SEQ ID NO:24.

In another aspect, the invention is directed to an isolated nucleic acid encoding the monoclonal antibody discussed above. In invention also includes a host cell that includes the nucleic acid encoding the monoclonal antibody discussed above.

The invention is also directed to a method for treating a disease associated with nicotine activity in a subject comprising administering a composition that includes the monoclonal antibody discussed above to the person in need thereof.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIGS. 1A-1B show selection of Fab clones specific to cotinine. (A) The reactivity of Fab clones retrieved following the sixth round of biopanning to cotinine was investigated by an enzyme immunoassay using a plate coated with each antigen and HRP-conjugated anti-human Fab antibody. (B) Cotinine-carrier conjugates, carriers, cotinine was used as an immunogen was investigated by a competitive enzyme immunoassay with free cotinine as described under "Materials and Methods" revealed that binding of Fab to the cotinine-BSA was inhibited in the presence of soluble cotinine. The concentration of used free cotinine was in the range of 0.001 ug/ml to 1000 ug/ml.

FIG. 2 shows sequences of heavy-chain and light-chain variable domains of anti-cotinine Fab clones. The selected Fab clones were subjected to DNA sequencing and then the identified sequences of heavy-chain ($V_H$) and light-chain ($V_L$) variable domains of anti-cotinine Fab clones were depicted as indicated. FR means framework region. CDR designates complementarity-determining region.

DETAILED DESCRIPTION OF THE PREFERRED EMBODIMENTS

Figure 3:
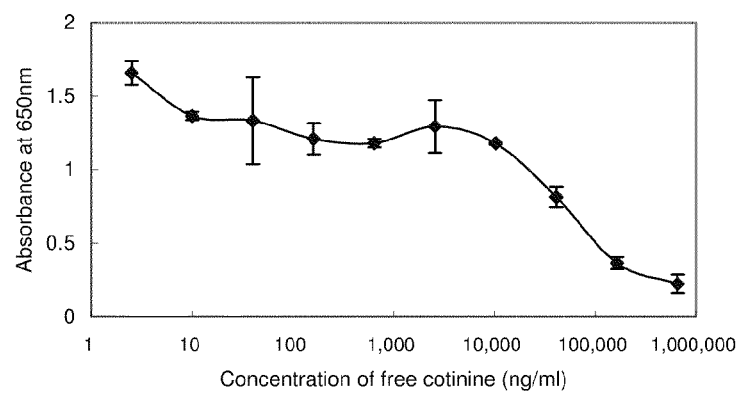
FIGS. 3A-3E show characterization of purified anti-cotinine Fab clones specific to cotinine. (A) An enzyme immunoassay using a plate coated with cotinine-BSA revealed that purified Fab bound to cotinine in a dose dependent manner. (B), (C), (D) Competitive enzyme immunoassay with free cotinine as described under "Materials and Methods" revealed that binding of purified Fab to cotinine-BSA was inhibited in the presence of soluble cotinine. The concentration of used free cotinine was in the range of 1 ng/ml to 1,000,000 ng/ml (B, C), 10 ng/ml to 10,000,000 (D). (B); A4, (C); B3, (D); C1. (E) Competitive enzyme immunoassay against free cotinine in non smoker's normal serum as described under "Materials and Methods" revealed that binding of purified Fab B3 to the cotinine-BSA was inhibited in the presence of soluble cotinine. The concentration of used free cotinine was in the range of 1 ng/ml to 1,000,000 ng/ml.

In the present application, "a" and "an" are used to refer to both single and a plurality of objects.
As used herein, the following abbreviations used shall have the following meaning: BSA, bovine serum albumin; KLH, keyholelimpet hemocyanine; OVA, ovalbumin; PCR, polymerase chain reaction; $CaCl_2$, calcium chloride; IgG, Immunoglobulin; $MgCl_2$, magnesium chloride; $NaN_3$, sodium azide; PAGE, polyacrylamide gel electrophoresis; PMSF, phenylmethanesulfonyl fluoride; PBS, phosphate-buffered saline; SDS, sodium dodecyl sulfate.

The term "vector", as used herein, which describes a vector capable of expressing a protein of interest in a suitable host cell, refers to a genetic construct that comprises essential regulatory elements to which a gene insert is operably linked in such a manner as to be expressed in a host cell.

Nicotine

Nicotine causes a short-term increase in blood pressure, heart rate and the flow of blood from the heart. It also causes the arteries to narrow. Further, intake of nicotine itself causes nicotine addiction. Therefore, the invention is directed to prophylactically treating cardiovascular diseases, which may be caused by nicotine.

Monoclonal Antibody to Cotinine and/or Nicotine

Although nicotine plays a key role in tobacco-mediated-nicotine addiction, it seemed it was less likely to induce immunogenicity. To overcome this hurdle, we had tried to generate the human/rabbit anti-cotinine recombinant monoclonal antibodies using phage display technology since cotinine has similarities with nicotine. Based on the results shown, this antibody has a strong affinity to cotinine and cross-reactivity with nicotine. In particular, the invention provides for an antibody that is particularly developed for nicotine by heavy chain CDR3 modification in order to treat nicotine addiction.

The use of immune therapy has become popular recently in case where the protein target of a disease has been determined. The highly specific targeting allowed by therapeutic antibodies results in virtually no side effects, even at relatively high doses. This also makes use of the antibodies' naturally inherent serum stability, providing the basis for a long-acting therapeutic molecule.

Antibody therapeutics generally falls into one of two categories that are not mutually exclusive. The first category is dependent on the variable region (target protein recognition portion) of the antibody. The specific epitope recognized by the antibody will allow the antibody to inhibit the binding of the target protein with other proteins (inhibitory or antagonistic effect) interfering with cell-cell interactions or terminating signal transduction through the target protein, or generate an artificial signal as a result of its binding with the target protein in the absence of a required secondary protein (activation or agonistic effect) as is the case of dimerization-dependent receptor signaling or receptor-dependent ligand mimicking. The second category depends on the constant region (Fc portion) of the antibody, that determines which, if any, immune effector functions will become activated as a result of the binding of the Fc portion of the antibody with its cognate Fc receptor present on the immune effector cells. The presence of a specific target protein on the surface of a target cell targets that cell for destruction by an effector function.

By developing an antibody that is highly specific for cotinine and/or nicotine, a therapeutic antibody has been created that inhibits or treats nicotine induced ill-effects, in particular those illnesses caused by addiction to nicotine.

In certain cases that deal with the pathogenic mechanisms of the mucosal immune system, antibodies may be administered orally or nasally. The mucosal immune system is unique, as tolerance is preferentially induced after exposure to antigen, and induction of regulatory T cells is a primary mechanism of oral tolerance. Orally administered antibody can be rapidly taken up by the gut-associated lymphoid tissue (GALT), where it exerts its immunologic effects. Oral administration of antibody can signal T cells in the gut in a fashion that delivers a weak but effective signal in enhancing the regulatory function of T cells. Oral administration of CD3 specific antibody has been demonstrated in experimental autoimmune encephalitis (EAE) model. These studies showed that the Fc portion of the CD3-specific antibody was not required. An orally administered F(ab')2 fragment of CD3-specific antibody suppressed EAE.

Conventional IgG antibodies are bivalent with the ability to bind to two antigens. This ability greatly increases their functional affinity and confers high retention time on many cell surface receptors and antigens. Anti-cotinine antibodies and anti-cotinine antibodies that also specifically bind nicotine may exist in many different antibody formats.

1. The anti-cotinine and/or anti-nicotine antibodies of the invention may be humanized monoclonal antibodies or human monoclonal antibodies. An entirely antigenic murine mAb becomes human friendly when small parts of the murine antibodies are engrafted onto human immunoglobulin molecules creating either chimeric antibodies where only the Fc part of the immunoglobulin molecule is human, or humanized antibodies where only the complementarity determining regions (CDR) of the immunoglobulin are murine and 90 to 95% of the molecule is human. In one respect, fully human monoclonal antibodies may be generated in transgenic mice by employing the HuMAb-Mouse (GenPharm-Medarex) or XenoMouse (Abgenix, Inc.) technology. Humanized antibodies include human immunoglobulins in which residues from a CDR of the recipient are replaced by residues from a CDR of a non-human species such as mouse, rat or rabbit having the desired specificity, affinity and biological function.

Human antibodies also can be produced using techniques such as phage display libraries (Hoogenboom and Winter, J. Mol. Biol, 1991, 227:381, Marks et al., J. Mol. Biol. 1991, 222:581). Methods for humanizing non-human antibodies are well known. Humanization can be performed following the method of Winter et al. (Jones et al., Nature, 1986, 321: 522; Riechmann et al., Nature, 1988, 332:323; Verhoeyen et al., Science, 1988, 239:1534) by substituting rodent CDR sequences or CDRs for the corresponding sequences of a human antibody. Such humanized antibodies are chimeric antibodies (U.S. Pat. No. 4,816,567). Typically, humanized antibodies are antibodies where CDR residues are substituted by residues from analogous sites in rodent antibodies.

2. The anti-cotinine and/or anti-nicotine antibodies of the invention may be single-chain variable fragment antibody (scFV). Recombinant approaches have led to the development of single chain variable fragment antibody (scFv). A monomeric scFv has a molecular mass of only about 30 kDa, which is expressed in a variety of systems as a single VL-VH pair linked by a Gly/Ser-rich synthetic linker (Berezov A. et al., 2001, J Med Chem 44:2565). When expressed in bacteria or eukaryotic cells, the scFv folds into a conformation similar to the corresponding region of the parental antibody. It was shown to retain comparable affinity to that of a Fab (Kortt et al., 1994, Eur J Biochem 221:151). ScFvs are amenable to various genetic modifications such as humanization and the production of fusion proteins to enhance their potential as therapeutic agents. For example, Pexelizumab, a humanized scFv that binds to the C5 component of complement has been shown to reduce myocardial infarctions during coronary artery bypass graft surgery (Varrier et al., 2004, JAMA 291: 2319).

Phage display method may be used to produce anti-cotinine and/or anti-nicotine scFv. In this method, large repertoires of antibody variable region cDNAs are collected from the B cells and combinations of VHs and VLs are expressed in the form of scFvs on the surface of filamentous bacteriophage. The phages that express scFvs are to be panned from antigen-coated plates. The affinity of the anti-anti-cotinine and/or anti-nicotine scFv may be improved by mutating the CDRs of the construct and then repeating the panning procedure.

3. The anti-cotinine and/or anti-nicotine antibodies of the invention may be monoclonal antibodies. Monoclonal antibodies are prepared using hybridoma methods, such as those described by Kohler and Milstein (Nature, 1975, 256:495). Mouse, rat, hamster or other host animals, is immunized with an immunizing agent to generate lymphocytes that produce antibodies with binding specificity to the immunizing antigen. In an alternative approach, the lymphocytes may be immunized in vitro.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Materials and Methods

Materials—Conjugate form of hapten-carrier (cotinine-KLH, -OVA, and -BSA), cotinine and nicotine were purchased from aBiox company (Portland, Oreg., USA). High fidelity Taq polymerase and Sfi I was purchased from Roche (Indianapolis, Ind., USA). T4 DNA ligase was purchased from Invitrogen (Carlsbad., Calif., USA). Other restriction endonucleases and appropriate buffers were purchased from New England Biolabs (NEB, Beverly, Mass., USA). Carbenicillin, tetracyclin, kanamycin, IPTG (Isopropyl-β-D-Thiogalactopyranoside), PEG 8000 (polyethylene glycol-8000), BSA (Bovine serum albumin), ABTS (2,2'-azino-bis (3-ethylbenzthiazoline-6-sulfonic acid), OPD (o-phenylenediamine dihydrochloride), RIBI's adjuvant (MPL+TDM+CWS (monophosphoryl lipid A+synthetic trehalose dicorynomycolate+cell wall skeleton) adjuvant for rabbits) were purchased from Sigma (St. Louis, Mo., USA). 96 well EIA plate was purchased from Corning (NY, USA). Dynabeads M-270 Epoxy was purchased from Dynal Biotech (Lake success, N.Y., USA). $H_2O_2$ was purchased from Duksan pure chemicals (Seoul, Kyung-gi, Korea). dNTP mix and First strand cDNA synthesis kit were purchased from Pharmacia (Piscataway, N.J., USA). DNA Gel extraction kit was purchased from Cosmo (Seoul, Kyung-gi, Korea). Plasmid mini-prep kit was purchased from Qiagen (Valencia, Calif., USA). TMB solution and BCA™ Protein Assay Kit was purchased from Pierce (Rockford, Ill., USA). Anti-human Fab specific antibody and anti-rabbit IgG antibody were purchased from Pierce (Rockford, Ill., USA), anti-M13 antibody was purchased from Amersham Pharmacia Biotech (Piscataway, N.J., USA).

Immunization—100 µg of cotinine-KLH, cotinine-OVA conjugate were respectively mixed in 2 ml of MPL+TDM+CWS adjuvant (Sigma, St. Louis, Mo.), incubated at 37° C. for 30 min, and then injected into New Zealand white rabbits. The injection was performed with cotinine-KLH for the beginning two times at 3 weeks intervals, after that six injection were performed alternatively with cotinine-KLH, cotinine-OVA. The last immunization was performed after 1 week from the eighth round of injection. The titre of serum antibody was determined by enzyme linked immunosorbent assay (ELISA) using horseradish peroxidase (HRP)—conjugated mouse anti-rabbit IgG polyclonal antibodies as a secondary antibody.

Construction of rabbit/human chimeric antibody library—The protocol is followed with a minor modification by Barbas et al., phage display. In brief, first-strand cDNA was synthesized from total RNA of spleen and bone marrow from immunized rabbit using the SuperScript™ 111 First-Strand synthesis system with oligo (dT) priming. To construct cotinine Fab library, PCR was performed with three steps of PCR. With the first round PCR, rabbit $V_L$ and $V_H$ were amplified from rabbit cDNA and human $C_L$ and $C_{H1}$ from a pComb3X expression vector containing a human Fab. Then, with the second round PCR, rabbit/human chimeric light chain and heavy chain were generated by combining rabbit $V_L$ with human $C_L$ and rabbit $V_H$ and with human $C_{H1}$ respectively using overlap extension PCR. In the third round of PCR, the chimeric light chain products and heavy chain products were joined by overlap extension PCR. The resulting Fab encoding library (1.4 ug) was digested with Sfi I (Roche, Indianapolis, Ind.), ligated into phagemid vector pComb3XSS (1.4 ug), and transformed into E. coli strain ER2738 cells (New England Biolabs) cultured in 10 ml of SB medium containing 10 ug/ml of tetracycline. The cultures were then incubated for 1 hr in a 37° C. shaker after the addition of 30 ug/ml of carbenicillin. VCSM13 helper phage ($>1 \times 10^{12}$ pfu/ml) 2 ml and 70 ug/ml of kanamycin were added to the cultures and incubated overnight at 37° C. Following centrifugation at 5,000 rpm for 15 min, the collected supernatant was incubated with 8 g of polyethylene glycol-8000 (PEG-8000) and 6 g of NaCl on ice for 30 min and then centrifuged at 9,000 rpm for 20 min. The phage pellet was resuspended in Tris-buffered saline (TBS) containing 3% (w/v) BSA and 0.02% $NaN_3$.

Selection of anti-cotinine specific antibody from antibody libraries—A total of six rounds of biopanning was performed by using paramagnetic bead (Dynabeads M-270 Epoxy, Dynal, Lake Success, N.Y.). For conjugation 9 ug of cotinine-BSA was incubated with $3 \times 10^7$ beads at 37° C. for 16 h. The beads were washed four times with 0.5% BSA/PBS and incubated with 3% BSA/PBS at room temperature for 1 h. The phage ($10^{11-13}$ pfu/ml) displaying naive/synthetic human Fab was incubated with the prepared beads at 37° C. for 2 h. Then the beads were washed with 0.5% PBST at room temperature for 10 min with gentle shaking, once at the first round of biopanning, three times at the second and third rounds, and five times during the fourth and fifth round. Throughout the biopanning process, a magnet (Dynal MPC) was used for separation of beads. After washing, bound phages were eluted by incubation with 50 ul of elution buffer (0.1 M glycine-HCl, pH 2.2) at room temperature for 5 min with gentle shaking. The eluate was used to transfect logarithmically growing ER2738 and the ER2738 harboring the phagemid library was grown by rescue of phagemid with helper phage VCSM13 for overnight amplification. Phage preparations were purified and concentrated by the addition of PEG and NaCl as described above (Barbas et al., phage display). This overall selection procedure was repeated up to 6 times and the washing steps were increased from 1 times in the first round to 5 in the second, third, and fourth round, 10 in the fifth round, and sixth round.

Overexpression and purification of anti-cotinine Fab—10 ng of phagemid DNA was transformed into Top10F' E. coli and the cells were grown in LB medium containing 50 mg/ml carbenicillin with constant shaking at 37° C. When the optical density at 600 nm reached 0.6, the cells were grown overnight at 30° C. After centrifugation at 15,000×g for 30 min, the collected supernatants were concentrated with Labscale TFF System (Milipore, Bedford, Mass.) and then incubated with anti-hemagglutin (HA) antibody conjugated protein A Sepharose. After washing with buffer containing 50 mM sodium, pH 8.2, the Fab was eluted with 0.1 M glycine, pH 2.2 and the fraction was immediately neutralized with 1 M Tris, pH 9.2 to adjust physiological pH. After dialysis in PBS overnight at 4° C., the concentration of the samples was calculated by measuring the optical density at 280 nm. The purity of the Fab was detected with Coomassie Brilliant staining.

Enzyme-linked immunosorbent assay (ELISA)—Cotinine-BSA dissolved in PBS, at a concentration of 5 ug/ml, were incubated respectively in the wells of a microtiter plate overnight at 4° C. After brief washing with PBS, the plate was blocked with 3% (w/v) BSA in PBS, incubated with the primary antibody for 1 hr at 37° C., and washed more than three times with PBS containing 0.05% Tween 20. The amount of Fab bound to the plate was detected by the application of horse radish peroxidase conjugated anti-HA mAb 3F10 antibody (Roche). Optical density was measured at 405 nm by a microtiter plate reader after incubation with ABTS or TMB substrate solution for 30 min at 37° C. For competition ELISA, cotinine or nicotine were incubated in a microtiter plate for 1 hr at 37° C. after antigen coating. The next procedures were similar as described above. In competition ELISA using the human serum, the solution containing Fab and cotinine were mixed with the same volume of human serum before being added to the plate.

Cell-free in vitro translation system—B3, C1 antibody was purified by cell-free in vitro translation system.

SDS-PAGE under nondenaturing conditions—20 ul of the purified cotinine Fab was separated by 10% SDS-PAGE. Routine staining was carried out with coomassie brilliant blue (CBB).

Example 2

Results

Generation and selection of cotinine-specific chimeric antibody—The aim of this study was to generate a recombinant antibody specific to cotinine. Thus, we first immunized cotinine-KLH, -OVA conjugate into rabbits. Enzyme immunoassay with rabbit sera collected after six times of immunization revealed that elevated antibody has affinity only to cotinine. After the eighth booster injection, total RNA was isolated from the spleen and the bone marrow of the immunized rabbits and subjected to cDNA synthesis. Using three steps of PCR, rabbit/human chimeric antibody library was generated and cloned into phagemid vector pComb3X, yielding the complexity of $6.0 \times 10^9$ independent transformants.

After six rounds of bio-panning on immobilized cotinine-BSA, 96 clones were randomly selected, rescued by the infection of helper phage, and tested for their reactivity to cotinine in phage enzyme immunoassay and competitive enzyme immunoassay against free cotinine. Four of the 96 selected clones showed strong reactivity to cotinine (FIG. 1A, 1B). These four individual clones were subsequently analyzed by DNA sequencing. They have different HCDR3 amino acid sequences and the sequences are shown in FIG. 2.

Biochemical and functional characterization of selected cotinine specific Fab—Following over-expression in E. coli and purification by anti-HA affinity column chromatography, 1 mg of anti-cotinine-specific Fab was finally obtained from 1 L of a shaking culture (clone ID A4). The Fab of the other three clones were purified by cell free in vitro translation system (clone ID B3, C1, and SUN10). Their purity was confirmed by SDS-PAGE and Coomassie blue staining (data not shown). Enzyme immunoassay experiments revealed that the purified antibody specifically bound to cotinine (FIG. 3A, 3B, 3C, 3D). Anti-cotinine Fab B3 clone of the three clones was also reactive toward cotinine in non smoker's normal serum (FIG. 3E).

Figure 4:
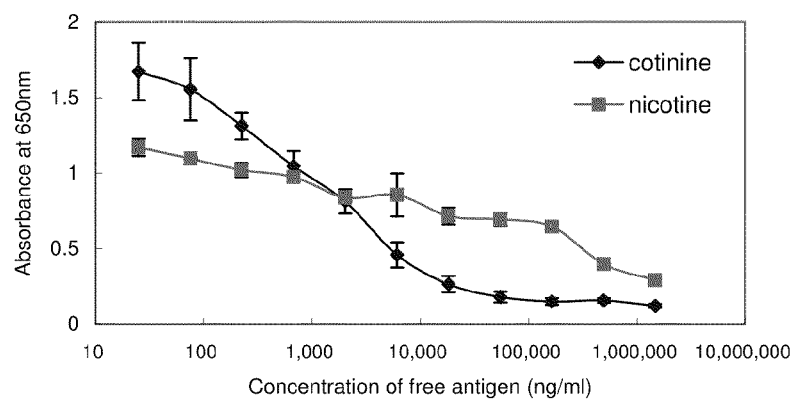
FIG. 4 shows cross reactivity of anti-cotinine Fab B3 with nicotine. Competitive enzyme immunoassay against free nicotine as described under "Materials and Methods" revealed that binding of purified anti-cotinine Fab B3 to the cotinine-BSA was also inhibited in the presence of soluble nicotine. The concentration of used used free nicotine was in the range of 10 ng/ml to 10,000,000 ng/ml.

Identification of the cross-reactivity against nicotine of selected anti-cotinine Fab—To identify the cross-reactivity against nicotine of purified anti-cotinine Fab B3, we performed competition ELISA with nicotine. This enzyme immunoassay experiment revealed that the purified anti-cotinine-specific Fab B3 also has cross-reactivity against nicotine (FIG. 4).

Example 3

Expression of Selected Antibodies

Positive phage clones obtained above were analyzed by DNA sequencing and chosen based on sequence alignment. See FIG. 2.

Table 1 below shows the CDR1, CDR2 and CDR3 regions for the heavy chain variable regions.

TABLE 1

Heavy chain variable region complementarity determining regions

| | CDR1 | CDR2 | CDR3 |
|---|---|---|---|
| A4 | SDWMN (SEQ ID NO: 1) | AVSRGSSGSTYYATWTK (SEQ ID NO: 2) | IPYFGYNNGDI (SEQ ID NO: 3) |
| B3 | SYDMI (SEQ ID NO: 7) | FISTGAATYYASWAR (SEQ ID NO: 8) | WDGSTIDNI (SEQ ID NO: 9) |

TABLE 1-continued

Heavy chain variable region complementarity determining regions

| | CDR1 | CDR2 | CDR3 |
|---|---|---|---|
| C1 | NYWMS (SEQ ID NO: 13) | DIHGNRGFNYH ASWAK (SEQ ID NO: 14) | ADDSGSHDI (SEQ ID NO: 15) |
| SUN10 | RDWMN (SEQ ID NO: 19) | AIGRSGDTYYATWAK (SEQ ID NO: 20) | IPYFGWNNGDI (SEQ ID NO: 21) |

Table 2 below shows the CDR1, CDR2 and CDR3 regions for the light chain variable regions.

TABLE 2

Light chain variable region complementarity determining regions

| | CDR1 | CDR2 | CDR3 |
|---|---|---|---|
| A4 | QSSQSLYGNEWLS (SEQ ID NO: 4) | RISTLAS (SEQ ID NO: 5) | AGGYNFGLFPFG (SEQ ID NO: 6) |
| B3 | QASQSVYKNNYLS (SEQ ID NO: 10) | LASTLAS (SEQ ID NO: 11) | AGYRYTTVDATAFG (SEQ ID NO: 12) |
| C1 | QSSQSVYSAKLS (SEQ ID NO: 16) | YGSTLAS (SEQ ID NO: 17) | QGTYYGPDWYFAFG (SEQ ID NO: 18) |
| SUN10 | QSSQSPYSNEWLS (SEQ ID NO: 22) | RISTLAS (SEQ ID NO: 23) | AGGYNFGLFPFG (SEQ ID NO: 24) |

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A monoclonal antibody that binds cotinine comprising the amino acid sequence of the heavy chain variable region having the CDR1 region as set forth in the SEQ ID NO:1, the CDR2 region as set forth in the SEQ ID NO:2 and the CDR3 region as set forth in the SEQ ID NO:3, and the amino acid sequence of the light chain variable region having the CDR1 region as set forth in the SEQ ID NO:4, the CDR2 region as set forth in the SEQ ID NO:5 and the CDR3 region as set forth in the SEQ ID NO:6.

2. A monoclonal antibody that binds cotinine comprising the amino acid sequence of the heavy chain variable region having the CDR1 region as set forth in the SEQ ID NO:7, the CDR2 region as set forth in the SEQ ID NO:8 and the CDR3 region as set forth in the SEQ ID NO:9, and the amino acid sequence of the light chain variable region having the CDR1 region as set forth in the SEQ ID NO:10, the CDR2 region as set forth in the SEQ ID NO:11 and the CDR3 region as set forth in the SEQ ID NO:12.

3. A monoclonal antibody that binds cotinine comprising the amino acid sequence of the heavy chain variable region having the CDR1 region as set forth in the SEQ ID NO:13, the CDR2 region as set forth in the SEQ ID NO:14 and the CDR3 region as set forth in the SEQ ID NO:15, and the amino acid sequence of the light chain variable region having the CDR1 region as set forth in the SEQ ID NO:16, the CDR2 region as set forth in the SEQ ID NO:17 and the CDR3 region as set forth in the SEQ ID NO:18.

4. A monoclonal antibody binds cotinine comprising the amino acid sequence of the heavy chain variable region having the CDR1 region as set forth in the SEQ ID NO:19, the CDR2 region as set forth in the SEQ ID NO:20 and the CDR3 region as set forth in the SEQ ID NO:21, and the amino acid sequence of the light chain variable region having the CDR1 region as set forth in the SEQ ID NO:22, the CDR2 region as set forth in the SEQ ID NO:23 and the CDR3 region as set forth in the SEQ ID NO:24.

* * * * *